United States Patent [19]
Isola et al.

[11] Patent Number: 6,011,181
[45] Date of Patent: Jan. 4, 2000

[54] TRIPHENYLPHOSPHINE OXIDE COMPLEX PROCESS

[75] Inventors: Arthur Mark Isola, Sheffield; Nicholas John Holman; Gerald Bernard Tometzki, both of Nottingham; John Paul Watts, Notts, all of United Kingdom; Stefan Koser, Ludwigshafen, Germany; Ralf Klintz, Grünstadt, Germany; Peter Münster, Römerberg, Germany

[73] Assignee: BASF Aktiengesellschaft, Ludwigshafen, Germany

[21] Appl. No.: 08/992,534

[22] Filed: Dec. 17, 1997

[30] Foreign Application Priority Data

Dec. 23, 1996 [DE] Germany .................. 9626746

[51] Int. Cl.⁷ .............................. C07F 9/53; C07D 475/08
[52] U.S. Cl. ............................... 568/14; 544/260
[58] Field of Search ................. 568/14, 878, 909.5, 568/918; 570/189, 217, 238; 544/260

[56] References Cited

U.S. PATENT DOCUMENTS

| 4,080,325 | 3/1978 | Ellard | 260/251.5 |
| 4,421,913 | 12/1983 | Ellard et al. | 544/260 |
| 5,292,973 | 3/1994 | Fukumoto et al. | 568/878 |

FOREIGN PATENT DOCUMENTS

| 1502339 | 3/1978 | United Kingdom . |
| 95/10521 | 4/1995 | WIPO . |
| 98/07724 | 2/1998 | WIPO . |

OTHER PUBLICATIONS

Lincoln et al., *Aust. J. Chem.*, 1981, vol. 34, pp. 283–289.
Camp et al., *Aust. J. Chem.*, 1988, vol. 41, pp. 1835–1839.
Itzstein et al., *Synthetic Comm.*, 1990, vol. 20, No. 13, pp. 2049–2057.
Kang et al., *Tet. Lett.*, vol. 37, No. 52, 1996, pp. 9317–9320.

*Primary Examiner*—Gary Geist
*Assistant Examiner*—Sreeni Padmanabhan
*Attorney, Agent, or Firm*—Keil & Weinkauf

[57] ABSTRACT

A process for reducing the level of tri-substituted phosphine, arsine and/or stibine oxide from a mixture comprising a desired product and at least one such oxide is provided, comprising the addition of a metal salt to the mixture to form a complex with the oxide, and removing the complex from the mixture. This process has particular utility for removing triphenylphosphine oxide from a mixture—a task that was previously hard to perform.

10 Claims, No Drawings

TRIPHENYLPHOSPHINE OXIDE COMPLEX PROCESS

PROCESS

The present invention relates to a process by which the level of oxides of trisubstituted phosphines, arsines and stibines in a mixture comprising a desired product and at least one such oxide can be reduced, thus enabling the desired product of the mixture to be more easily isolated.

Elements of group V of the periodic table, such as phosphorus, arsenic and antimony, are able to form tri-substituted compounds, such as tri-substituted phosphines, arsines and stibines. Tri-substituted phosphines, arsines and stibines, in which the substituents are organic moieties, have a wide application in chemistry, for example as reducing agents in certain reactions, the result of which is the formation of their respective oxide. Furthermore, the oxides of tri-substituted phosphines, arsines and stibines have some utility themselves as reagents or catalysts. However, the oxides of tri-substituted phosphines, arsines and stibines, for example triphenylphosphine oxide, are frequently difficult to separate from other substances.

It will be understood that for the remainder of this document, the term "trisubstituted phosphine, arsine and/or stibine" refers to tri-substituted phosphine, arsine and/or stibine in which the substituents are organic moieties.

Many chemical reactions involve the formation of an oxide of a tri-substituted phosphine, arsine or stibine, for example Mitsunobu reactions, wittig formation of olefins, certain deoxygenations of epoxides, sulphoxides and amine oxides, and certain conversions of alcohols into alkyl halides. A disadvantage of these reactions is the formation of oxidised tri-substituted phosphine, arsine or stibine, which is difficult to remove from the desired product. It is often necessary to purify the desired product by means of column chromatography, which is impractical and inefficient for large scale syntheses.

The Mitsunobu reaction is a condensation reaction between an alcohol and an acidic component using a redox couple. Examples of suitable acidic components include phenols, carboxylic acids, N-hydroxyimides, sulphonic acids or metal salts thereof, cyclic imides, hydrazoic acid or metal salts thereof, thiocarboxylic acids, and p-dicarbonyl compounds (such as β-diketones and p-ketoesters). The reaction may be intermolecular or intramolecular. Often, the redox couple of a triaryl- or trialkylphosphine and a dialkyl azodicarboxylate is used in such reactions. It is a very good method for producing chiral compounds because it results in generally good yields with high stereoselectivity (inversion), and is relatively simple to carry out since the alcohol activation and displacement reactions take place in a single procedure—usually at room temperature.

A useful redox couple for Mitsunobu reactions is diisopropyl azodicarboxylate (DlAD) and triphenylphosphine, which leads to the production of triphenylphosphine oxide. This oxidised reducing agent is difficult to remove from the desired product, and several attempts have been made to overcome this disadvantage. One solution to the problem is to use for example a basic phosphine, such as diphenyl(2-pyridyl)phosphine or (4~dimethylaminophenyl) diphenylphosphine~ as the reducing agent in the redox couple. This facilitates product isolation since the resulting phosphine oxide is removed by aqueous acid washing. However, these basic phosphines may not be suitable for the synthesis of some chiral compounds since the acid washing may cause racemisation of the chiral centre, and some products may be soluble in acid so that separation from the phosphine oxide would not be achieved by acid washing. Furthermore, use of these basic phosphines is not commercially viable on a production scale. In addition, the yield can be substantially reduced by using a reducing agent other than triphenylphosphine. Polymer-bound phosphines may also be used to avoid the formation of triphenylphosphine oxide. However, these phosphines are expensive and the reaction is significantly slower so that time and cost efficiency are compromised.

The wittig reaction is the reaction between an aldehyde or ketone and an ylid, resulting in the formation of an olefin and the oxide of a tri-substituted phosphine, arsine or stibine. It is a very useful reaction because it can be conducted under mild conditions. Triphenylphosphine is often used as the basis for forming the ylid, the subsequent reaction of which with an aldehyde or ketone results in the formation of triphenylphosphine oxide. Again, difficulties are experienced in isolating the desired product from the unwanted oxide. This can be avoided by using a different phosphine such as 4~(diphenylphosphino)benzoic acid, the oxide of which is soluble in aqueous base and therefore easily removed from the neutral reaction conditions. However, this may have a detrimental effect on yield. Also, some products may be soluble in aqueous base so that separation from the phosphine oxide would not be achieved by washing with aqueous base.

Other reactions, such as the deoxygenation of epoxides to olefins, sulphoxides to sulphides and amine oxides to amines using tri-substituted phosphines, arsines and stibines, and the conversion of alcohols into alkyl halides using a tri-substituted phosphine, arsine or stibine/halogen reagent system (for example dihalotriphenylphosphorane, preferably dibromo, or triphenylphosphine and a halogen, preferably bromine or chlorine), also result in tri-substituted phosphine, arsine or stibine oxide formation and, therefore, product isolation problems. Similar solutions to those discussed for Mitsunobu and wittig reactions may be applied in an attempt to facilitate desired product separation, but may have similar disadvantages.

Some reactions involve the use of an oxide of a tri-substituted phosphine, arsine or stibine as a catalyst. The oxide remains unchanged after the reaction, and is present in the product mixture. An example of such a reaction is use of a phosphine, arsine or stibine oxide as a catalyst for the condensation of carboxylic acids with 1,2-diaminoarenes in the presence of trifluoromethanesulphonic anhydride to form 2-substituted benzimidazoles. The same problems of desired product isolation are faced in this situation as in those reactions discussed above.

Some reactions involve the use of an oxide of a tri-substituted phosphine, arsine or stibine as a reagent. In such reactions there may be unreacted trisubstituted phosphine, arsine or stibine oxide present in the product mixture. The same problems of desired product isolation are faced in this situation as in those reactions discussed above.

However, we have now surprisingly found a means of reducing the level of tri-substituted phosphine, arsine or stibine oxide in a mixture, which means is inexpensive, quick, requires mild conditions and neutral pH, and is very easy to carry out both on a laboratory scale and on a production scale. This new process allows the efficient reduction of the level of unwanted phosphine, arsine or stibine oxide from product mixtures, therefore facilitating isolation of the desired product, and making the reactions described above easier to handle and more commercially viable, particularly on an industrial scale.

Accordingly, the present invention provides a process for reducing the level of tri-substituted phosphine, arsine and/or stibine oxide in a mixture comprising a desired product and at least one such oxide, said process comprising a) the addition of a metal salt to form a complex or complexes with the tri-substituted phosphine, arsine or stibine oxide or oxides, and b) the separation of the resultant complex or complexes from the remainder of the mixture, with the proviso that when the mixture is the result of a Mitsunobu reaction, and one of the starting materials of said reaction is a compound of formula A, then the other starting material is other than a compound of formula B, such compounds being defined as follows:

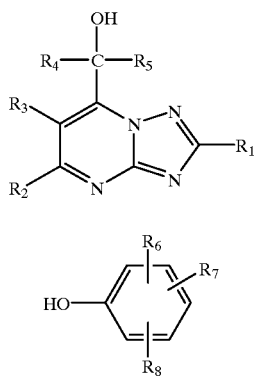

in which $R_1$ represents H or one of the following groups (optionally substituted with one or more of halo, cyano, hydroxy or amino): $C_{1-6}$alkyl, $C_{1-6}$alkoxy or $C_{1-6}$alkanoyl;

$R_2$ and $R_3$ independently represent H or one of the following groups (optionally substituted with one or more of halo, cyano, hydroxy or amino): $C_{1-6}$alkyl, $C_{1-6}$alkoxy, $C_{1-6}$alkanoyl, $C_{1-6}$alkylthio, $C_{1-6}$alkylsulphinyl or $C_{1-6}$alkylsulphonyl;

$R_4$ and $R_5$ independently represent H, $G_{1-6}$alkyl or $R_4$ and $R_5$ combined together with the carbon atom to which they are attached represent $C_{3-6}$cycloalkylidene (each alkyl or cycloalkylidene being optionally substituted with one or more of halo, cyano, hydroxy, amino or $C_{1-6}$alkyl) and $R_6$, $R_7$ and $R_8$ independently represent H, halo, hydroxy, mercapto, nitro, cyano or one of the following groups (optionally substituted with one or more of halo, cyano, hydroxy or amino; and any nitrogen atom being optionally substituted with one or more $C_{1-6}$alkyl): $C_{1-6}$alkyl, $C_{1-6}$alkanoyl, $C_{1-6}$alkoxy, $C_{2-6}$alkoxycarbonyl, carboxy, $C_{1-6}$alkanoyloxy, $C_{1-6}$alkylthio, $C_{1-6}$alkylsulphinyl, $C_{1-6}$alkylsulphonyl, $C_{1-6}$alkyl- sulphonylamino, sulphamoyl, carbamoyl, $C_{2-6}$alkylcarbamoyl or $C_{1-6}$alkanoylamino.

It will be appreciated by those skilled in the art that the mixture in which the tri-substituted phosphine, arsine or stibine oxide level is reduced may be a product mixture in which the oxide has been formed as part of the reaction, or it may be a mixture comprising tri-substituted phosphine, arsine or stibine oxide which has been added as such and was not formed as part of the reaction.

Preferably, the mixture is a product mixture resulting from a Mitsunobu reaction, a Wittig reaction, a deoxygenation reaction using a tri-substituted phosphine, arsine or stibine, a conversion of an alcohol into an alkyl halide using a tri-substituted phosphine, arsine or stibine/halogen system, or a mixture comprising tri-substituted phosphine, arsine or stibine oxide which has been added as such and was not formed as part of the reaction.

When the reaction is a Mitsunobu reaction, it will be understood that a redox couple comprising an oxidising agent and a reducing agent has been involved. The reducing agent has been oxidised (to form a tri-substituted phosphine, arsine or stibine oxide) and the oxidising agent has been reduced as a result of the reaction. The reducing agent may be selected from a tri-substituted phosphine, arsine or stibine, preferably a tri-substituted phosphine. It will further be understood that the reduced oxidising agent may be removed from the desired product either before or after steps a) and b) are carried out. Preferably the reduced oxidising agent is removed after steps a) and b) are carried out.

The mixture is preferably in an inert diluent. The term "inert diluen~ means a diluent commonly used by those skilled in the art which is inert to the reaction conditions. Preferably the inert diluent is a solvent or mixture of solvents selected from tetrahydrofuran, diethyl ether, 1,4-dioxane, toluene, acetonitrile, dichloromethane, dimethylformamide, diisopropyl ether, t-butyl methyl ether and ethyl acetate.

The separation of the resultant complex or complexes from the remainder of the mixture [step b) of the present invention] may be achieved by one of the following methods. In cases where the complex precipitates out of the solution, the separation may be achieved by filtration, decantation, or centrifugation. Preferably, separation is achieved by filtration. When filtration is used it may be desirable to use a filter aid such as a diatomaceous earth, for example Celite®. It will be understood that the desired product may then be obtained from the filtrate for example by evaporation or crystallisation. Alternatively, if the complex is soluble in the inert diluent, and therefore does not precipitate out of the solution, the inert diluent may be removed by evaporation and replaced by a solvent, in which the complex and the remainder of the mixture have different solubilities. Suitably the solvent is selected from water, methanol, ethanol and/or propan-2-ol and/or any of the inert diluents listed previously herein, or it may be a mixture of any of these. When a desired product is more soluble than the complex, the insoluble complex can be separated and the desired product obtained as described above. Alternatively, when the complex is more soluble than the desired product, the insoluble desired product can then be separated by filtration, decantation, or centrifugation.

Optionally, further purification of a desired product may be carried out after steps a) and b). Further purification may comprise, for example trituration with a suitable solvent, for example tetrahydrofuran, diethyl ether, a $C_{1-4}$ alcohol (e.g. methanol, ethanol, propanol or butanol), 1,4-dioxane, toluene, acetonitrile, dichloromethane, dimethylformamide, diisopropyl ether, t-butyl methyl ether, ethyl acetate and water or mixtures thereof preferably for example methanol, ethanol, propanol or propan-2-ol or mixtures thereof, more preferably a propanol, most preferably propan-2-ol, and/or crystallisation from such a suitable solvent. Preferably, the further purification comprises trituration with propan-2-ol or crystallisation from propan-2-ol. It will be appreciated by those skilled in the art that steps a) and b) of the process may be carried out iteratively if desired. Preferably, steps a) and b) of the process are carried out until the level of tri-substituted phosphine, arsine and/or stibine oxide has been reduced sufficiently to enable the desired product to be isolated by the further purification described above, in a form which is substantially free of tri-substituted phosphine, arsine and/or stibine oxide. Preferably, the level of tri-substituted phosphine, arsine and/or stibine oxide is reduced to 15% of the mixture or less. Most preferably, the level of tri-substituted phosphine, arsine and/or stibine oxide is reduced to substantially 0% (wherein no tri-substituted phosphine, arsine and/or stibine oxide is detectable by Gc or HPLC analysis).

When the mixture is a product mixture in which the oxide has been formed as part of the reaction, it will be appreciated that the metal salt of step a) may be added during or after the reaction, subsequent to an inert diluent change after completion of the reaction, or after removal of another component of the mixture, for example when the product mixture is the result of a Mitsunobu reaction, after removal of the reduced oxidising agent. Preferably, the metal salt is added after the reaction.

Preferably, when step a) is carried out after the reaction, the mixture is brought to a temperature in the range 0 to 120° C., preferably at 20 to 120° C., most preferably the mixture is heated under reflux at the boiling point temperature of the inert diluent, for up to 16 hours, preferably for up to 6 hours, more preferably for 1 to 4 hours, subsequent to the addition of the metal salt, then the mixture is cooled to a temperature in the range −10° C. to ambient temperature.

It will be appreciated that the phrase "addition of a metal salt" in step a) is intended to include the addition of a metal salt and/or the addition of reactants suitable for the formation of a metal salt in situ, for example a metal and an acid, or a metal oxide and an acid. The present invention therefore includes both the above additions.

Preferably the metal salt is added in a quantity ranging from 0.25 to 5 molar equivalents of the tri-substituted phosphine, arsine or stibine or tri-substituted phosphine, arsine or stibine oxide, more preferably in a quantity ranging from 1.5 to 3 molar equivalents of the tri-substituted phosphine, arsine or stibine or trisubstituted phosphine, arsine or stibine oxide.

The metal salt may be a halide (for example fluoride, chloride, bromide or iodide), sulphate, nitrate, perchlorate, bicarbonate, carbonate, acetate, citrate or benzoate salt of an alkali, alkaline earth, group lb, transition or lanthanide metal, or a solvate thereof, for example a hydrate or organic solvate. Preferably the metal is selected from lithium, sodium, potassium, magnesium, calcium, barium, strontium, samarium(lll), zinc, iron (II), iron (III), manganese (II), cobalt (II), cobalt (III), nickel, copper (I), and copper (II). Preferably, the metal salt is a halide salt of lithium, magnesium, calcium, manganese (II), iron (II), iron (III), copper (I), copper (II), zinc, or cobalt (II). More preferably the salt is the chloride salt or bromide salt. Most preferably the metal salt is selected from magnesium chloride, magnesium bromide diethyl etherate, and cobalt (II) chloride hexahydrate. It is desirable that the metal salt is low in cost, toxicity, Lewis acidity and oxidising ability. Especially preferred is magnesium chloride.

The salt may be added to the mixture in the form of powder, pellets, or a solution or slurry in an inert diluent. In one preferred form magnesium chloride is added as a powder.

The tri-substituted phosphine, arsine or stibine may be any of those known in the art, but is preferably a phosphine. For example, the tri-substituted phosphine may be selected from tris($C_{1-4}$-alkyl)phosphine, triphenylphosphine, tris(3-chloro-phenyl)phosphine, tris(4-chlorophenyl)phosphine, tris(3-methylphenyl)phosphine, tris(4-methylphenyl) phosphine, tris(3-methoxyphenyl)phosphine, tris(4-methoxy-phenyl)phosphine, phenoxydiphenylphosphine and diphenoxyphenylphosphine.

The tri-substituted phosphine, arsine or stibine oxide may be any of those known in the art, but is preferably a phosphine oxide. For example, the trisubstituted phosphine oxide may be selected from tris($C_{1-4}$-alkyl)phosphine oxide, triphenylphosphine oxide, tris(3-chlorophenyl)phosphine oxide, tris(4-chlorophenyl)-phosphine oxide, tris(3-methylphenyl)phosphine oxide, tris(4-methylphenyl)-phosphine oxide, tris(3-methoxyphenyl)phosphine oxide, tris(4-methoxyphenyl)-phosphine oxide, phenoxydiphenylphosphine oxide and diphenoxyphenylphosphine oxide.

Suitably, the level of tri-substituted phosphine, arsine and/or stibine oxide in the mixture is reduced by at least 20%. Preferably the level of tri-substituted phosphine, arsine and/or stibine oxide is reduced by at least 30%. More preferably the level of tri-substituted phosphine, arsine and/or stibine oxide is reduced by at least 50%. Especially preferably, the level of tri-substituted phosphine, arsine and/or stibine oxide is reduced by at least 70%. Most preferably the level of tri-substituted phosphine, arsine and/or stibine oxide is reduced by at least 85%. The percentage reduction is calculated by comparing the % of oxide present, by normalisation by gas-liquid chromatography, in the mixture before and after the process of the present invention is carried out.

The invention will now be illustrated by the following non-limiting examples. The examples are illustrative only, and have not necessarily been carried out under optimal conditions. The final product of each example was characterised using one or more of the following techniques: elemental analysis; infra-red spectroscopy; nuclear magnetic resonance spectroscopy; gas-liquid chromatography (Gc); and high performance liquid chromatography (HPLC). Temperatures are given in degrees Celsius. Under Gc analysis, triphenylphosphine oxide and the complexes comprising triphenylphosphine oxide may have the same retention time so that figures for percentage triphenylphosphine oxide levels after complexation may refer to total triphenylphosphine oxide levels (both free and complexed).

EXAMPLES

ETHER FORMATION VIA MITSUNOBU REACTION

1) Removal of triphenylphosphine oxide from 4-chlorophenyl 1-phenylethyl ether reaction mixture using $MgCl_2$ (2 eq)

Diisopropyl azodicarboxylate (1.23 g) in tetrahydrofuran (2 ml) was added dropwise over 1 hour to a mixture of 1-phenylethanol (0.74 g), triphenylphosphine (1.62 g) and 4-chlorophenol (0.78 g) in tetrahydrofuran (12 ml) which was stirred under nitrogen at 0–5° C. The mixture was stirred for a further 16 hours at ambient temperature. The solvent was removed in vacuo from a sample of the mixture, and the residue was analysed by Gc for triphenylphosphine oxide content.

Magnesium chloride (1.14 g) was added to the remaining mixture. The mixture was heated under reflux for 2 hours, then cooled to 0° C. for one hour then filtered, and the filter pad washed with tetrahydrofuran (10 ml). The solvent was removed from the filtrate in vacuo and the resulting residue extracted with ethyl acetate (20 ml). The extract was filtered, washed with water (20 ml) and the solvent then removed in vacuo to yield a residue (1.58 g) which was analysed for triphenylphosphine oxide content.

% Triphenylphosphine oxide content by normalisation by Gc analysis

| before complexation: | 48.9% |
|---|---|
| after complexation: | 14.3% |

2) Removal of triphenylphosphine oxide from 4-chlorophenyl 1-phenylethyl ether reaction mixture using CoCl$_2$.6H$_2$O (1 eq)

A Mitsunobu reaction to form 4-chlorophenyl 1-phenylethyl ether was carried out in a similar manner to that described in Example 1 above, using diisopropyl azodicarboxylate (12.3 g) in tetrahydrofuran (20 ml), 1-phenylethanol (7.45 g), triphenylphosphine (15.99 g) and 4-chlorophenol (7.80 g) in tetrahydrofuran (120 ml). The solvent was removed Th vacuo from a sample of the mixture, and the residue was analysed by Gc for triphenylphosphine oxide content. A sample (54 ml) of the mixture was taken, and the solvent was removed in vacuo. Ethanol (100 ml) and cobalt chloride hexahydrate (9.52 g) were added. The mixture was heated under reflux for 2 hours, then cooled to 0° C. for one hour then filtered and the filter pad washed with ethanol (10 ml). The solvent was removed from the filtrate in vacuo and the residue dried in a desiccator over 2 days and then extracted with ethyl acetate (60 ml). The extract was filtered, washed with water (40 ml), and the solvent then removed Th vacuo to yield a residue which was analysed by Gc for triphenylphosphine oxide content.

% Triphenylphosphine oxide content by normalisation by Gc analysis

| before complexation: | 51.1% |
|---|---|
| after complexation: | 4.5% |

3) Removal of triphenylphosphine oxide from 4-chlorophenyl 1-phenylethyl ether reaction mixture using CuCl$_2$.2H$_2$O (2 eq)

A sample (54 ml) of the mixture from the Mitsunobu reaction described in Example 2 was taken, and the solvent was removed in vacuo. Ethanol (100 ml) and copper (II) chloride dihydrate (6.82 g, 2 eq) were added. The mixture was heated under reflux for 2 hours, cooled to 0° C. for one hour then filtered and the filter pad washed with ethanol (10 ml). The solvent was removed from the filtrate in vacuo and the residue dried in a desiccator over 2 days, and then extracted with ethyl acetate (70 ml). The extract was filtered, washed with water (40 ml), and the solvent then removed in vacuo to yield a residue which was analysed by Gc for triphenylphosphine oxide content.

% Triphenylphosphine oxide content by normalisation by Gc analysis

| before complexation: | 51.1% |
|---|---|
| after complexation: | 17.0% |

4) Removal of triphenylphosphine oxide from 4-chlorophenyl 1-phenylethyl ether reaction mixture using CaCl$_2$ (2 eq)

A Mitsunobu reaction to form 4-chlorophenyl 1-phenylethyl ether was carried out in a similar manner to that described in Example 1 above, using diisopropyl azodicarboxylate (40.7 g) in tetrahydrofuran (60 ml), 1-phenylethanol (22.36 g), triphenylphosphine (52.8 g) and 4-chlorophenol (23.53 g) in tetrahydrofuran (360 ml). The solvent was removed Th vacuo from a sample of the mixture, and the residue was analysed by Gc for triphenylphosphine oxide content.

Calcium chloride (4.4 g) was added to a sample (50 ml) of the mixture. The mixture was heated under reflux for 2 hours, then cooled to 0° C. for 0.5 hours, then filtered and the filter pad washed with tetrahydrofuran (10 ml). The solvent was removed from the filtrate in vacuo and the residue extracted with toluene (20 ml). The extract was filtered, washed with water (20 ml), dried (MgSO$_4$) and the solvent then removed in vacuo. The residue was analysed by Gc for triphenylphosphine oxide content.

% Triphenylphosphine oxide content by normalisation by Gc analysis

| before complexation: | 48.4% |
|---|---|
| after complexation: | 30.2% |

5) Removal of triphenylphosphine oxide from 4-chlorophenyl 1-phenylethyl ether reaction mixture using LiCl (2 eq)

Lithium chloride (1.7 g) was added to a sample (50 ml) of the mixture from the Mitsunobu reaction described in Example 4. The mixture was heated under reflux for 2 hours, then cooled to 0° C. for 16 hours, filtered and the filter pad washed with tetrahydrofuran (10 ml). The solvent was removed from the filtrate in vacuo and the resulting residue was extracted with toluene (20 ml). The extract was filtered, washed with water (20 ml), dried (MgSO$_4$) and the solvent then removed in vacuo. The residue was analysed by Gc for triphenylphosphine oxide content.

% Triphenylphosphine oxide content by normalisation by Gc analysis

| before complexation: | 48.4% |
|---|---|
| after complexation: | 32.8% |

6) Removal of triphenylphosphine oxide from 4-chlorophenyl 1-phenylethyl ether reaction mixture using MgF$_2$ (2 eq)

Magnesium fluoride (2.5 g) was added to a sample (50 ml) of the mixture from the Mitsunobu reaction described in Example 4. The mixture was heated under reflux for 2 hours, cooled to 0° C. for 16 hours, filtered and the filter pad washed with tetrahydrofuran (10 ml). The solvent was removed from the filtrate in vacuo and the resulting residue was extracted with toluene (20 ml). The extract was filtered, washed with water (20 ml), dried (MgSO$_4$) and the solvent then removed in vacuo. The residue was analysed by Gc for triphenylphosphine oxide content.

% Triphenylphosphine oxide content by normalisation by Gc analysis

| before complexation: | 48.4% |
|---|---|
| after complexation: | 37.6% |

7) Removal of triphenylphosphine oxide from 4-chlorophenyl 1-phenylethyl ether reaction mixture using MgBr$_2$ (OEt$_2$) (2 eq)

Magnesium bromide diethyl etherate (10.33 g) was added to a sample (55 ml) of the mixture from the Mitsunobu reaction described in Example 4. The mixture was heated under reflux for 2 hours, then cooled to 0° C. for 16 hours filtered and the filter pad washed with tetrahydrofuran (10 ml). The solvent was removed from the filtrate in vacuo and the residue was extracted with toluene (20 ml). The extract was filtered, washed with water (20 ml), dried (MgSO$_4$) and the solvent then removed in vacuo. The residue was analysed by Gc for triphenylphosphine oxide content.

% Triphenylphosphine oxide content by normalisation by Gc analysis

| before complexation: | 48.4% |
|---|---|
| after complexation: | 3.3% |

8) Removal of triphenylphosphine oxide from 4-chlornphenyl 1-phenylethyl ether reaction mixture using anhydrous FeCl$_2$ (1 eq)

Anhydrous ferrous chloride (2.54 g) was added to a sample (55 ml) of the mixture from the Mitsunobu reaction described in Example 4. The mixture was heated under reflux for 2 hours, then cooled to 0° C. for 16 hours and filtered, and the filter pad washed with tetrahydrofuran (10 ml). The solvent was removed from the filtrate in vacuo and the resulting residue was extracted with toluene (20 ml). The extract was filtered, washed with water (20 ml), dried (MgSO$_4$) and the solvent then removed in vacuo. The residue was analysed by Gc for triphenylphosphine oxide content.

% Triphenylphosphine oxide content by normalisation by Gc analysis

| before complexation: | 48.4% |
|---|---|
| after complexation: | 29.1% |

ESTER FORMATION VIA MITSUNOBU REACTION

9) Removal of triphenvlphosphine oxide from 1-([1.2.4] triazolo-[1,5-a]pyrimidin-7-yl)ethyl benzoate reaction mixture using MgCl$_2$ (2 eq)

Diisopropyl azodicarboxylate (1.23 g) in tetrahydrofuran (2 ml) was added dropwise over one hour to a stirred mixture of 1-([I,2,4]-triazolo[1,5-a]pyrimidin-7-yl)ethanol (1.00 g), triphenylphosphine (1.62 g) and benzoic acid (0.74 g) in tetrahydrofuran (12 ml) under nitrogen at 0–5° C. Stirring was continued for 16 hours at ambient temperature. The solvent was removed Th vacuo from a sample of the mixture, and the residue was analysed by Gc for triphenylphosphine oxide content.

Magnesium chloride (1.14 g) was added to the remaining mixture. The mixture was heated under reflux for one hour, then cooled to 0° C. for one hour, filtered, and the filter pad washed with tetrahydrofuran (5 ml). The solvent was removed from the filtrate in vacuo and the residue extracted with toluene (20 ml). This extract was filtered. The combined insoluble residues were extracted with ethyl acetate (20 ml) and this extract filtered. These two extracts were combined, washed with water (20 ml) and the solvents then removed in vacuo to yield a residue. The residue was analysed by Gc for triphenylphosphine oxide content.

lsopropanol (5 ml) was added to the residue and the mixture allowed to stand at 0–5° C. for 3 days. The mixture was filtered and the solid washed with cold (0° C.) isopropanol (2 ml) to give 1-([1,2,4]triazolo[1,5-a]pyrimidin-7-yl) ethyl benzoate.

% Triphenylphosphine oxide content by normalisation by Gc analysis

| before complexation: | 54.4% |
|---|---|
| after complexation: | 20.5% |
| after isopropanol trituration: | 0.2% |

C—N BOND FORMATION VIA MITSUNOBU REACTION

10) Removal of triphenylphosphine oxide from N-(1-phenylethvl)phthalimide reaction mixture using MgCl$_2$ (2 eq)

Diisopropyl azodicarboxylate (2.46 g) in tetrahydrofuran (4 ml) was added dropwise over one hour to a stirred mixture of 1-phenylethanol (1.49 g), triphenylphosphine (3.24 g) and phthalimide (1.79 g) in tetrahydrofuran (25 ml) under nitrogen at 0–5° C. Stirring was continued for 3 days at ambient temperature. The solvent was removed in vacuo from a sample of the mixture, and the residue was analysed by Gc for triphenylphosphine oxide content.

Magnesium chloride (2.29 g) was added, and the mixture was heated under reflux for 3 hours, allowed to stand at ambient temperature for 16 hours, then cooled to 0° C. for one hour and filtered. The solvent was removed from the filtrate in vacuo and the resulting residue extracted with ethyl acetate (20 ml). The extracted was filtered, washed with water (20 ml), dried (MgSO$_4$) and the solvent then removed in vacuo to yield a residue which was analysed by Gc for triphenylphosphine oxide content.

% Triphenylphosphine oxide content by normalisation by Gc analysis

| before complexation: | 58.8% |
|---|---|
| after complexation: | 19.1%. |

OLEFIN FORMATION VIA WITTIG REACTION

11) Removal of triphenylphosphine oxide from 4-[(4-benzyloxy-3-methoxy)phenylibut-3-en-2-one reaction mixture using MgCl$_2$ (2.1 eq)

A mixture of O-benzylvanillin (2.25 g) and acetylmethylene-triphenylphosphorane (3.00 g) in toluene (20 ml) was heated on a steam bath for 16 hours. The solvent was removed in vacuo from a sample and the residue was analysed by Gc for triphenylphosphine oxide content.

Magnesium chloride (1.86 g) was added, and the mixture was heated under reflux for 2 hours, then cooled to 0° C. for 16 hours, filtered, and the filter pad washed with tetrahydrofuran (20 ml). The solvent was removed from the filtrate in vacuo and the resulting residue stirred with toluene (40 ml) for 0.5 hours. The mixture was filtered, and the filter pad washed with toluene (20 ml). The filtrate was washed with water (20 ml) and the solvent then removed in vacuo to yield a residue, a sample of which was analysed by Gc for triphenylphosphine oxide content.

lsopropanol (5 ml) was added to the residue, and the mixture cooled to 0° C. for 2 hours. The precipitate was collected by filtration to yield 4-[(4-benzyloxy-3-methoxy) phenyl]but-3-en-2-one (0.927 g) which was analysed by Gc for triphenylphosphine oxide content.

% Triphenylphosphine oxide content by normalisation by Gc analysis

| | |
|---|---|
| before complexation: | 53.5% |
| after complexation: | 7.0% |
| after isopropanol trituration: | 0.2% |

12) Removal of triphenylphosphine oxide from (2E,4E,6E)-2,7-bis-(5,5-dimethyl-1,3-dioxan-2-yl)octa-2,4,6-triene reaction mixture using $MgCl_2$ (2 eq)

(E)-3-(5,5-Dimethyl-1,3-dioxan-2-yl)but-2-enal (9.2 g) was added to a mixture of (E)-[3-(5,5-dimethyl-1,3-dioxan-2-yl)-but-2-en-1-yl]triphenylphosphonium chloride (23.3 g), sodium methoxide solution (2 ml 30% in methanol) and dichloromethane (150 ml). Sodium methoxide solution (10 g; 30% in methanol) was then added dropwise. The mixture was heated under reflux for one hour, allowed to cool to ambient temperature, then extracted with water. The solvent was removed from the extract in vacuo and the resulting residue dissolved in tetrahydrofuran (100 ml). The solvent was removed in vacuo and the resulting residue dissolved in tetrahydrofuran (100 ml).

Magnesium chloride (9.5 g) was added and the resulting suspension was heated under reflux for 30 minutes, then cooled to ambient temperature, filtered, and the filter pad washed with tetrahydrofuran. Magnesium chloride (2.9 g) was added to the filtrate, the mixture heated under reflux for 30 minutes, cooled to ambient temperature, filtered, and the filter pad washed with tetrahydrofuran. The solvent was removed from the filtrate in vacuo to yield a residue (19.6 g) which was analysed by 13C-NMR for triphenylphosphine oxide content.

% Triphenylphosphine oxide content by 13C-NMR after complexation: 20%

13) Removal of triphenylphosphine oxide from ethyl 2-chloro-3-(2-chloro-5-nitrophenyl)prop-2-enoate reaction mixture using $MgCl_2$ (2 eq)

A mixture of [chloro(ethoxycarbonyl)methylene] triphenylphosphorane (5.0 g) and 2-chloro-5-nitrobenzaldehyde (2.4 g) in tetrahydrofuran (80 ml) was stirred for 30 minutes at 5° C. Magnesium chloride (2.5 g) was added and the resulting suspension heated under reflux for 30 minutes, then cooled to ambient temperature and filtered. Magnesium chloride (0.75 g) was added to the filtrate and the resulting mixture heated under reflux for 30 minutes, then cooled to ambient temperature and filtered. The filter pad was washed with tetrahydrofuran. The solvent was removed from the combined filtrates in vacuo and the resulting residue was extracted with toluene (100 ml). This extract was washed with water (3×30 ml), dried ($Na_2SO_4$) and the solvent removed in vacuo to yield a residue (3.1 g).

% Triphenylphosphine oxide content by i3C-NMR after complexation: 25%

14) Removal of triphenylphosphine oxide from 3-[2-(3.4-dichlorophenyl)-ethenyl]indole-5-carbonitrile reaction mixture using $MgCl_2$ (2.2 eq)

n-Butyllithium (2.5M solution in hexanes, 3.6 ml) was added to a stirred solution of (3,4-dichlorobenzyl) triphenylphosphonium bromide (4.4 g) in tetrahydrofuran (20 ml) at 0–5° C. under nitrogen and the mixture then stirred at ambient temperature for 30 minutes. 3-Formylindole-5-carbonitrile (1.0 g) was added in portions over 5 minutes. The resulting mixture was stirred for 25 minutes, diluted with tetrahydrofuran (10 ml) and then heated under reflux for 2.5 hours. water (20 ml) followed by ethyl acetate (25 ml) were added to the cooled mixture and the layers were separated. The ethyl acetate layer was washed with water (2×30 ml) and then brine (30 ml), then dried ($MgSO_4$) and the solvent removed in vacuo to give a residue which was analysed by NMR for triphenylphosphine oxide content.

A mixture of this residue, magnesium chloride (1.8 g, 2.2 eq) and ethyl acetate (30 ml) was stirred and heated under reflux for 45 minutes and then cooled to 0° C. The mixture was filtered and the filter bed washed with ethyl acetate (30 ml). The combined filtrates were washed with water/brine (2/1, 2×30 ml) and dried ($MgSO_4$) and the solvent then removed in vacuo to give a residue (2.59 g) which was analysed by NMR for triphenylphosphine oxide content.

% Triphenylphosphine oxide content by NMR

| | |
|---|---|
| before complexation: | 56.5% |
| after complexation: | 9% |

TRIPHENYLPHOSPHINE-MEDIATED DEOXYGENATION OF AN EPOXIDE TO AN OLEFIN

15) Removal of triphenylphosphine oxide from N-(prop-2-en-1-yl)-phthalimide reaction mixture using $MgCl_2$ (1 eq)

A stirred mixture of N-(2,3-epoxypropyl)phthalimide (2.03 g) and triphenylphosphine (2.62 g) was heated in an oil-bath at 150° C. under nitrogen for 4 hours. The mixture was cooled to ambient temperature for 16 hours, then a sample was analysed by Gc for triphenylphosphine oxide content.

Tetrahydrofuran (15 ml) and magnesium chloride (0.96 g) were added. The mixture was heated under reflux for 2 hours, cooled to 0° C. for 1 hour, filtered and the filtered pad washed with tetrahydrofuran (10 ml). The solvent was removed from the filtrate in vacuo and the resulting residue extracted with ethyl acetate (20 ml). The extract was filtered, washed with water (20 ml) and the solvent then removed in vacuo to yield a residue which was analysed by Gc for triphenylphosphine oxide content.

% Triphenylphosphine oxide content by normalisation by Gc analysis

| | |
|---|---|
| before complexation: | 67.1% |
| after complexation: | 25.6%. |

CONVERSION OF AN ALCOHOL INTO AN ALKYL HALI DE VIA DIBROMOTRIPHENYLPHOSPHORANE SYSTEM

16) Removal of triphenylphosphine oxide from 1-bromo-2-(3.4-dimethoxyphenyl)-ethane reaction mixture using $MgCl_2$ (1 eq)

A mixture of 2-(3,4-dimethoxyphenyl)ethyl alcohol (3.64 g) and dibromotriphenylphosphorane (8.44 g) in acetonitrile (30 ml) was stirred at 0–5° C. for 2.5 days. The solvent was removed Th vacuo and the residue was dissolved in ethyl acetate (50 ml) and water (20 ml). The organic layer was separated and dried ($MgSO_4$), and the solvent then removed in vacuo. A sample was analysed by Gc for triphenylphosphine oxide content.

Magnesium chloride (1.9 g) and tetrahydrofuran (15 ml) were added to the residue. The mixture was heated under reflux for 3 hours, left to stand for 16 hours at ambient temperature, cooled to 0° C. for 3 hours, filtered and the filter pad washed with tetrahydrofuran (10 ml). The solvent was removed from the filtrate in vacuo and the residue extracted with ethyl acetate (20 ml). The extract was filtered, washed with water (20 ml), and the solvent then removed in vacuo to yield a residue which was analysed by Gc for triphenylphosphine oxide content.

% Triphenylphosphine oxide content by normalisation by Gc analysis

| before complexation: | 74.3% |
|---|---|
| after complexation: | 34.1% |

ITERATIVE REMOVAL OF TRIPHENYLPHOSPHINE OXIDE FROM A MITSUNOBU REACTION MIXTURE

17) Removal of triphenylphosphine oxide from 4-chlorophenyl 1-phenylethyl ether reaction mixture using $MgF_2$ (2 eq) iteratively Diisopropyl azodicarboxylate (10.1 g) in tetrahydrofuran (50 ml) was added dropwise over one hour to a stirred mixture of 1-phenylethanol (6.1 g), triphenylphosphine (13.1 g) and 4-chlorophenol (6.4 g) in tetrahydrofuran (100 ml) under nitrogen at 0° C. The mixture was stirred for a further 16 hours at ambient temperature. The solvent was removed Th vacuo from a sample of the mixture, and the residue was analysed by Gc for triphenylphosphine oxide content.

Magnesium fluoride (6.23 g) was added to the remaining mixture. The mixture was heated under reflux for 2 hours, then cooled to 0° C. for one hour and filtered. The solvent was removed from the filtrate in vacuo and the resulting residue dissolved in toluene (100 ml). The solvent was removed in vacuo from a sample of the mixture, and the residue was analysed by Gc for triphenylphosphine oxide content.

Magnesium fluoride (6.3 g) was added to the toluene solution, the mixture heated on a steam bath for 2 hours then cooled to ambient temperature. The mixture was allowed to stand at 5° C. for 5 days and then filtered. The filtrate was washed with water (2×50 ml) and the solvent then removed in vacuo to yield a residue (14 g) which was analysed by Gc for triphenylphosphine oxide content.

% Triphenylphosphine oxide content by normalisation by Gc analysis

| before complexation: | 71.4% |
|---|---|
| after 1st complexation: | 51.1% |
| after 2nd complexation: | 43.4% |

TRIPHENYLPHOSPHINE OXIDE AS A CATALYST IN A REACTION TO PRODUCE 2-SUBSTITUTED BENZIMIDAZOLES

18) Removal of triphenylphosphine oxide from 2-phenylbenzimidazole reaction mixture using $MgCl_2$ (2 eq)

A solution of trifluoromethanesulphonic anhydride (1.57 ml) in dichloromethane (20 ml) was added dropwise to a stirred solution of triphenylphosphine oxide (5.56 g) in dichloromethane (20 ml) at 0–5° C. The mixture was stirred for 20 minutes. A mixture of 1,2-diaminobenzene (0.44 g) and benzoic acid (0.61 g) in dichloromethane (20 ml) was added and the mixture stirred for 2 hours. The mixture was washed with sodium hydrogen carbonate solution (50 ml), dried over magnesium sulphate, and the organic solvent was removed in vacuo. A sample of the residue was analysed by Gc for triphenylphosphine oxide content.

The residue was dissolved in tetrahydrofuran (30 ml) and magnesium chloride (4 g) was added. The mixture was heated under reflux for 2 hours, then cooled to 0° C. and filtered. The solvent was removed from the filtrate in vacuo and the residue was partitioned between ethyl acetate (50 ml) and water (20 ml). The organic layer was dried over magnesium sulphate, then the solvent was removed in vacuo to yield a residue which was analysed for triphenylphosphine oxide content.

% Triphenylphosphine oxide content by normalisation by Gc analysis

| before complexation: | 86.5% |
|---|---|
| after complexation: | 42.6% |

We claim:

1. A process for reducing the level of tri-substituted phosphine, arsine and/or stibine oxide in a mixture comprising a desired product and at least one such oxide, said process comprising
   a) the addition of a metal salt to form a complex or complexes with the tri-substituted phosphine, arsine or stibine oxide or oxides, and
   b) the separation of the resultant complex or complexes from the remainder of the mixture,
with the proviso that when the mixture is the result of a Mitsunobu reaction, and one of the starting materials of said reaction is a compound of formula A, then the other starting material is other than a compound of formula B, such compounds being defined as follows:

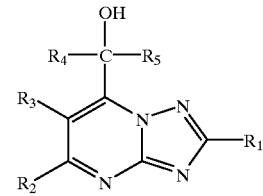

A

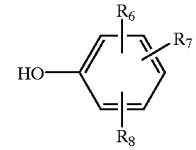

B in which $R_1$ represents H or one of the following groups (optionally substituted with one or more of halo, cyano, hydroxy or amino): $C_{1-6}$alkyl, $C_{1-6}$alkoxy or $C_{1-6}$alkanoyl;

$R_2$ and $R_3$ independently represent H or one of the following groups (optionally substituted with one or more of halo, cyano, hydroxy or amino): $C_{1-6}$alkyl, $C_{1-6}$alkoxy, $C_{1-6}$alkanoyl, $C_{1-6}$alkylthio, $C_{1-6}$alkylsulphinyl or $C_{1-6}$alkylsulphonyl;

$R_4$ and $R_5$ independently represent H, $C_{1-6}$alkyl or $R_4$ and $R_5$ combined together with the carbon atom to which they are attached represent $C_{3-6}$cycloalkylidene (each alkyl or cycloalkylidene being optionally substituted with one or more of halo, cyano, hydroxy, amino or $C_{1-6}$alkyl) and $R_6$, $R_7$ and $R_8$ independently represent H, halo, hydroxy, mercapto, nitro, cyano or one of the following groups (optionally substituted with one or more of halo, cyano, hydroxy or amino; and any nitrogen atom being optionally substituted with one or more $C_{1-6}$alkyl): $C_{1-6}$alkyl, $C_{1-6}$alkanoyl, $C_{1-6}$alkoxy, $C_{2-6}$alkoxycarbonyl, carboxy, $C_{1-6}$alkanoyloxy, $C_{1-6}$alkylthio, $C_{1-6}$alkylsulphinyl, $C_{1-6}$alkylsulphonyl, $C_{1-6}$alkylsulphonylamino, sulphamoyl, carbamoyl, $C_{2-6}$alkylcarbamoyl or $C_{1-6}$alkanoylamino.

2. The process of claim 1 in which the level of tri-substituted phosphine, arsine and/or stibine oxide in the mixture is reduced by at least 20%.

3. The process of claim 1 in which the level of tri-substituted phosphine, arsine and/or stibine oxide in the mixture is reduced sufficiently to enable the desired product to be isolated by further purification in a form which is substantially free of tri-substituted phosphine, arsine and/or stibine oxide.

4. The process of claim 3 in which the level of tri-substituted phosphine, arsine and/or stibine oxide is reduced to 15% of the mixture or less.

5. The process of claim 3 in which the further purification comprises an additional process step of trituration or crystallisation.

6. The process of claim 1 in which the trisubstituted phosphine, arsine or stibine oxide is tri-phenylphosphine oxide.

7. The process of claim 1 in which the metal salt is magnesium chloride, magnesium bromide or cobalt (II) chloride or a solvate or hydrate thereof.

8. The process of claim 1 in which the mixture is a product mixture resulting from a Mitsunobu reaction, a Wittig reaction, a deoxygenation reaction using a tri-substituted phosphine, arsine or stibine, a conversion of an alcohol into an alkyl halide using a tri-substituted phosphine, arsine or stibine/halogen system, or a condensation of a carboxylic acid with a 1,2-diaminoarene in the presence of trifluoromethanesulphonic anhydride.

9. The process of claim 1 in which the metal salt of step
 a) is added after the reaction involving the starting materials.

10. The process of claim 1 in which the metal salt is added in a quantity ranging from 0.25 to 5 molar equivalents of the tri-substituted phosphine, arsine or stibine or tri-substituted phosphine, arsine or stibine oxide.

* * * * *